United States Patent [19]

Lehtinen

[11] Patent Number: 5,733,564

[45] Date of Patent: Mar. 31, 1998

[54] METHOD OF TREATING ENDO-OSTEAL MATERIALS WITH A BISPHOSPHONATE SOLUTION

[75] Inventor: Risto Tapani Lehtinen, Paattinen, Finland

[73] Assignee: Leiras Oy, Turku, Finland

[21] Appl. No.: 525,561

[22] PCT Filed: Apr. 12, 1994

[86] PCT No.: PCT/FI94/00136

§ 371 Date: Sep. 19, 1995

§ 102(e) Date: Sep. 19, 1995

[87] PCT Pub. No.: WO94/23770

PCT Pub. Date: Oct. 27, 1994

[30] Foreign Application Priority Data

Apr. 14, 1993 [FI] Finland ................. 931657

[51] Int. Cl.$^6$ .......................... A61F 2/02
[52] U.S. Cl. ........................ 424/423; 623/16
[58] Field of Search ................... 424/423; 623/16

[56] References Cited

U.S. PATENT DOCUMENTS 4,763,788  8/1988  Jönéus et al. ............. 206/438
4,820,698  4/1989  Degenhardt et al. ......... 514/102
5,403,829  4/1995  Lehtinen et al. ........... 514/102

OTHER PUBLICATIONS

Chemical Abstract vol. 78, No. 25, Jun. 25, 1973 Jung, A. et al. abstract No. 155727, Calcif. Tissue Res. 1973 11 (4) 269-80.

Primary Examiner—Carlos A. Azpuru
Attorney, Agent, or Firm—Adduci, Mastriani & Schaumberg, LLP

[57] ABSTRACT

An endo-osteal material which includes an endo-osteal material treated with a solution of a bisphosphonate of formula (1) wherein X is H, OH, Cl, F or a methyl group and Y is Cl, OH, —(CH$_2$)$_2$—N(CH$_3$)—(CH$_2$)$_4$—CH$_3$, —(CH$_2$)$_n$—CH$_3$ or —(CH$_2$)$_n$—NH$_2$, where n is zero or an integer being 1 to 8, —NHZ, where Z is pyridinyl or cycloheptyl, SZ', where Z' is pyridinyl or chlorosubstituted phenyl or Y is a pyridinylsubstituted lower alkyl chain; or a non-toxic, pharmaceutically acceptable salt or ester thereof dissolved in an appropriate solvent.

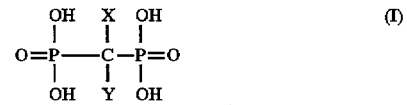

11 Claims, 15 Drawing Sheets

METHOD OF TREATING ENDO-OSTEAL MATERIALS WITH A BISPHOSPHONATE SOLUTION

BACKGROUND OF THE INVENTION

This invention relates to the use of bisphosphonates for the treatment of endo-osteal materials including implants to be used in surgery before their introduction into the human body. The invention concerns particularly the addition of a certain amount of a bisphosphonate to the sterile preservation medium for the endo-osteal materials.

In recent years intensive studies have been made on artificial endo-osteal materials, especially implants, to be introduced in the human body such as artificial joints, fixation plates in skeleton, hips and dental implants. Substantial efforts have been made with respect to materials which give high mechanical strength as well as good biological affinity.

Surgical techniques involving the use of endo-osteal prostheses including implants (screw implants, blade implants, pin implants etc) into bone tissue are extensively used in orthopaedic and dental surgery as a result of the progress made in somatological engineering.

Endo-osteal prostheses can roughly be divided into two groups: those comprising a metallic substrate on the one hand and ceramics and glass-ceramics (bioceramics) on the other hand. Metallic prostheses possess excellent strength properties but rather poor biocompatibility. Titanium and its alloys are the most frequently used metallic prostheses in both orthopaedic and dental surgery. In order to enhance the osseointegration and bone bonding process the metallic substrate is normally plasma-spray coated e.g. with apatite or hydroxyapatite to promote the bone bonding process. As examples of endo-osteal orthopaedic prostheses can mentioned Tricon-M and Allopro knee prostheses, Ortholoc tibial prosthesis and Monk, DF-80 and Authopor hip prostheses. Among the frequently used metal substrate implants in the dental field can be mentioned pure titanium implants (Nobelpharma, Swede-Vent®, IMZ). Among coated metallic substrate implant can be mentioned Bonefit®, a titanium substrate with titanium plasma coating; Steri-Oss®, a hydroxyapatite-coated metal alloy substrate and Calcitec, a hydroxyapatite coated titanium substrate. The ceramic implants are e.g. based on polycristalline aluminium oxide, $Al_2O_3$ (Frialit). Glass-ceramics and bioceramics include various compositions of glasses, ceramics and glass-ceramics having ability to bond to bone.

Endo-osteal materials to be introduced in the human body must be preserved strictly under sterile conditions before use. The preservation can take place under dry conditions or in a sterile solution. All the dental implants used are packed in sterile glass syringes. These syringes are either empty or contain physiologic saline solution. Dental implants are normally packaged in small ampouls in some milliliters of sterile sodium chloride solution. The hip prostheses are packed in sterile containers, all parts in their separate containers without any liquid.

The preservation of the prostheses and implants before their use is not just a problem relating to sterility. It is known that the biocompability of an implant is highly associated with the surface property of the material. It is therefore of great importance that the surface layer is carefully controlled and specified at the atomic level. Two implants initially manufactured from the same material can acquire completely different bioactivity properties depending on how the material is treated. Sterilization can for example vary between two similar implants and thus result in totally different biocompability for the two similar implants. The problem relating to the risk of contamination of the surface of the implant resulting in inactivation of the implant surface has been realized, and suggestions to overcome the problem have been made. U.S. Pat. No. 4,712,681 describes a method of packaging artifical implants in sterile and contamination-free manner according to which the implant is packaged in an inner capsule made of the same material as the implant itself. U.S. Pat. No. 4,763,788 suggests a rather similar solution of the contamination problem; it represents a modification of the double capsule system presented in U.S. Pat. No. 4,712,681.

The sensitivity of the implant surface to particles in the surrounding has thus been regarded as a difficulty to be overcome.

This invention is based on the idea to take advantage of the sensivity phenomenon and bring the surface of the endo-osteal material in close contact with agents having a positive influence on the biocompatibility of the endo-osteal material. This is practically carried out by adding a biocompatibility promoting agent to a solution in which the endo-osteal material is going to be preserved before its use.

SUMMARY OF THE INVENTION

According to one aspect of the invention an effective amount of a bisphosphonate is added to the solution to be used for the preservation of endo-osteal materials such as artificial joints, hip prostheses, fixation plates, dental and other implants. The use of endo-osteal prostheses having been stored in this manner optionally in combination with a systemic bisphosphonate therapy is strongly believed to result in a much lower failure rate compared to the situation where no bisphosphonate is added to the preservation solution for the endo-osteal prosthesis.

DETAILED DESCRIPTION OF THE PREFERRED EMBODIMENTS

Figure 1:
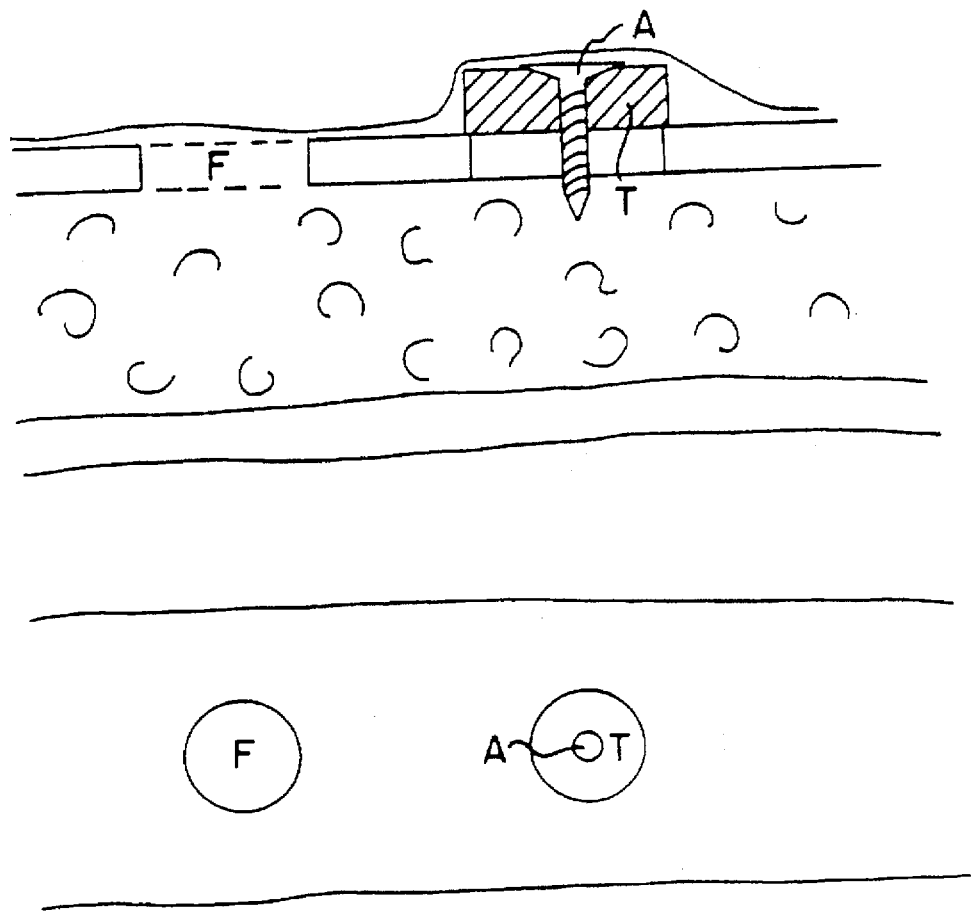
FIG. 1 represents a rabbit tibia having an implant screw A, a transplant T and a donor cavity F. The upper drawing of the Figure depicts a cross section and the lower drawing shows the tibia as seen from above.

Bisphosphonates are synthetic organic compounds structurally related to pyrophosphate in that the pyrophosphate P—O—P-bond is replaced by a P—C—P-bond. In contrast to pyrophosphate, bisphosphonates are resistant to enzymatic hydrolysis in osseous tissue. The bisphosphonates are potent inhibitors of bone resorption and they have been successfully used in the treatment of hypercalcemia caused by various reasons. A great number of bisphosphonates have been studied, but only clodronate, etidronate and pamidronate have reached wider clinical use.

The main effect of the bisphosphonates is their ability to inhibit bone resorption, but contrary to the effect on mineralization, the mechanism involved is cellular (Fleisch H, Drugs 1991; 42:919–44). These different effects vary greatly according to the structure of the individual bisphosphonate compound. The half-life of circulating bisphosphonates is very short, in the order of minutes to hours. Of a given dose, 20 to 50% is taken up by the skeleton, the rest being excreted in the urine. The half-life in bone is far longer and depends upon the turnover rate of the skeleton itself.

A review (Mian M et al., Int J Clin Pharmacol Res. 1991; 11:107–14) of 126 publications on clinical studies concerning the use of clodronate in the therapy of bone disease, involving 1930 patients, in order to evaluate the tolerability and the effects following short- and long-term administration of this drug, indicates that clodronate therapy does not have any clinically significant side-effects and confirm its tolerability and safety.

Of the many compounds belonging to the bisphosphonate family, clodronate has been widely used in hypercalcemia and osteolysis of malignancy (Bonjour J P and Rizzoli R, Calcif Tissue Int 1990; 46 Suppl: 20–25). All published reports indicate that clodronate can normalize plasma calcium in the majority of hypercalcemic, rehydrated cancer patients in whom increased bone resporption is the prevailing disturbed calcium flux (Fleisch H, Drugs 1991; 42:919–44).

Various phosphonate compounds are also reported in the patent literature as being useful in the treatment of anomalous mobilization and deposition of calcium phosphate salts (bone mineral) in mammals. Reference is made to U.S. Pat. Nos. 3,678,164; 3,662,066; 3,553,314; 3,553,315; 3,584,124; 3,584,125 and 3,641,246. U.S. Pat. No. 3,683,080 discloses the use of clodronate and various other phosphonates for the treatment of anomalous calcification involving soft tissues and arthritic conditions. U.S. Pat. No. 4,234,645 discloses clodronate as useful in the treatment of various collagen diseases.

As discussed above, bisphosphonates are well documented with respect to their ability to inhibit bone resorption in connection with various diseases. The use of these compounds to promote bone tissue formation subsequent to surgical operations relating to endo-osteal prosthesis such as hip prostheses, plates used in internal rigid fixation and various kinds of implantations; osteomyelitis after decortication of necrotics from the mandible or bone transplantations has, however, never been suggested. Particularly in dental implantation surgery, patients with severe atrophy of the mandibular alveolar process are difficult to treat by conventional implant techniques. At the abutment connection operation mobile fixtures are found frequently. About half of the number of recorded failures occurred under the healing period (Adell R et al., Int J Oral & Maxillofac Surg 1990, 5:347–359). Autogenous bone grafts used for severely resorbed ridge augmentation usually resorb to a considerable extent (Baker R D et al., J Oral Surg 1970; 37:486–89).

The effect of clodronate on hydroxyapatite has been extensively studied. Although the effect of clodronate on hydroxyapatite is well documentated, the use of clodronate or other bisphosphonates to preserve hydroxyapatite coated or otherwise coated endo-osteal prostheses including implants has never been suggested. Neither has been suggested the use of bisphosphonates to activate the uncoated metal surface of such prostheses or implants.

The present invention relates to a method of treating endo-osteal materials to be used in surgery for sterile and biocompatibility promoting storage characterized in the embedding the endo-osteal material in an aqueous solution comprising an effective amount of a compound of formula (I)

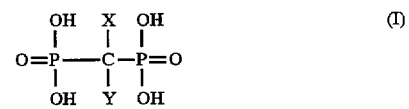

wherein X is H, OH, Cl, F or a methyl group and Y is Cl, OH, —(CH$_2$)$_2$—N(CH$_3$)—(CH$_2$)$_4$—CH$_3$, —(CH$_2$)$_n$—CH$_3$ or —(CH$_2$)$_n$—NH$_2$, where n is zero or an integer being 1 to 8, —NHZ, where Z is pyridinyl or cycloheptyl, SZ', where Z' is pyridinyl or chlorosubstituted phenyl or Y is a pyridinylsubstituted lower alkyl chain; or a non-toxic, pharmaceutically acceptable salt or ester thereof, after which the endo-osteal material is either removed from the solution, dried and sterilized, or sealed in a vessel comprising a bisphosphonate solution and sterilized.

The invention concerns also the packaged endo-osteal material to be used in surgery for sterile and biocompatibility promoting storage characterized in that said endo-osteal material treated with a solution of a bisphosphonate of the formula (I) or a non-toxic, pharmaceutically acceptable salt or ester thereof dissolved in an appropriate solvent.

The term "endo-osteal material" shall be understood to include all kinds of endo-osteal prostheses and parts thereof to be introduced in the human body, e.g. artificial joints, hip prostheses, fixation plates for the skeleton and implants, especially dental implants.

Particularly valuable members of formula (I) for the purpose of this invention are clodronate, where X and Y both are Cl; pamidronate, where X is OH and Y is —(CH$_2$)$_2$—NH$_2$; alendronic acid, where X is OH and Y is —(CH$_2$)$_3$—NH$_2$; neridronic acid, where X is OH and Y is —(CH$_2$)$_5$—NH$_2$; risedronic acid, where X is OH and Y is is 3-pyridinylmethyl; tiludronate, where X is H and Y is 4-chlorophenylthio; YM-175, where X is H and Y is cycloheptylamino; BM-210995, where X is OH and Y is —(CH$_2$)$_2$—N(CH$_3$)—(CH$_2$)$_4$—CH$_3$; and etidronate, where X is methyl and Y is OH. The most preferable compound for the purpose of the invention is clodronate or its pharmaceutically acceptable salts or esters.

The pharmaceutically acceptable salts and esters useful in the practice of this invention can be described by formula (II)

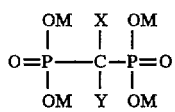

wherein X and Y are as defined above and M is hydrogen, a pharmaceutically acceptable cation, preferably an alkali metal cation such as sodium or potassium, or an alkyl or aryl moiety, e.g. an alkyl of 1 to 4 carbon atoms or phenyl.

The suitable amount of bisphosphonate to be added to the treatment solution ranges from 0.5 to 100 mg/ml, preferably 1 to 10 mg/ml.

The treatment can be performed for example as follows: After manufacturing the endo-osteal prostheses they are imersed in a solution of 1 to 6 mg/ml of a bisphosphonate for a period ranging from about 20 minutes to 7 days. After that the endo-osteal prostheses can be dried and sterilized by gamma-radiation and stored in dry condition before their use. Alternatively the endo-osteal prostheses can be stored in the same or a similar bisphosphonate solution as that in which they were immersed. In this case the bisphosphonate solution is sterilized by gamma-radiation.

The treatment with bisphosphonates apply to endo-osteal prostheses having a ceramic surface as well as those having no ceramic surface.

The inventive idea has been verified by animal and clinical tests. According to two separate studies with clodronate disodium, the methods and results of which are presented in detail below, the effect of clodronate on bone tissue formation is demonstrated.

In the first test, the effect of clodronate on bone regeneration was tested in rabbit tibia. An experimental model involving free bone transplantation to the tibia was developed. The tests revealed that clodronate had a positive effect on bone regeneration in the donor cavity and in the free bone grafts transplanted using a titanium screw. Clodronate-treated tibias were more quickly and more extensively vascularized than the control tibias.

The results of human studies, where the patients had an extra implant that was removed after a certain period of time, demonstrated that clodronate-medicated patients exhibited a more rapid bone formation than the unmedicated control group.

Hydroxyapatite and bisphosphonbate molecules form a surface and not a chemical bond. In the surface there is a place for calcium atoms. Thus the calcium concentration is high. The composition of hydroxyapatite and bisphosphonate forming a layer on the surface of the endo-osteal prosthesis or other implant is helpful in bone regeneration after surgery.

The effect of bisphosphonates for the treatment of implants has also been studied in tests reported below.

Because of the close structural and pharmacological relationship between clodronate and its analogues as represented by formula (I) above it is justified to believe that the remaining members of formula (I) also are effective to promote the biocompatibility of endo-osteal prostheses including implants during their storage.

EXPERIMENTS

I. Effect of Clodronate on Bone Regeneration in Rabbits

The aim of the study was to determine whether clodronate had a positive effect on vascularization and bone formation in the tibia of a rabbit in which bone was transplanted with the aid of a titanium screw.

Materials and Methods

Sixteen skeletally mature (3.5–3.9 kg) New Zealand white male rabbits were used. The animals were divided into two groups. Each group consisted of eight animals (16 tibiae). One group received clodronate disodium (Bonefos®, Leiras Oy, Finland) 25 mg/kg i.m. twice a week. The other group (control) was untreated.

The rabbits were anaesthetized with an i.m. injection of 2.8 mg of Ketalar® (Parke-Davis, Spain) and 2.0 ml of Rompun® (Bayer, Germany).

The proximal ends of both tibiae were exposed and the periosteum removed from the operative area. A piece of cortical bone 4 mm across was removed using a triphan bore. A 0.6 mm titanium implant screw (Filpin, Filpol Dental, Ireland) was screwed through the piece. The piece, perforated with the implant, was screwed into place 3 mm above the donor cavity. Reference is made to FIG. 1 representing the rabbit tibia, where A means the implant, T the transplant and F the donor cavity. The upper drawing of the Figure represents the cross section and the lower drawing the tibia as seen from above.

Figure 2:
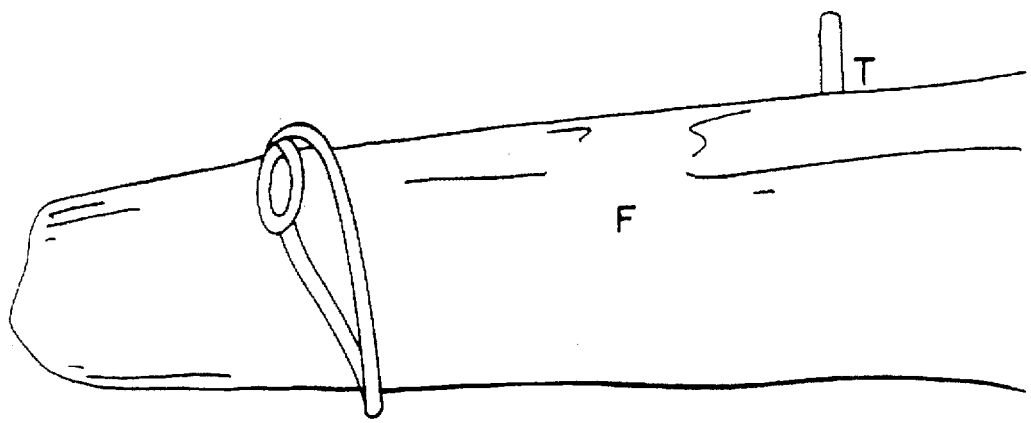
FIG. 2 is a lateral roentgen picture of a rabbit tibia, wherein the letters A, T and F have the same meaning as in FIG. 1.

The animals were divided into two groups: microangiography was performed on eight animals and histological staining specimens was carried out from the other eight animals. Roentgenological examinations with two steel wires with knots twisted around the tibiae to determine the exact positions of implant and donor cavity were performed. Reference is made to FIG. 2, which discloses a lateral roentgen picture of tibia in the operation area. The letters A, T and F have the same meaning as in FIG. 1.

Histological Evaluation

Eight animals were killed for histological evaluations at various times after implantation: after 14 days (2 rabbits), 21 days (4 rabbits) and 35 days (2 rabbits). The number of control and clodronate-treated animals was the same each time.

Tibiae were fixed with 5% phosphate-buffered formalin and toluine blue staining and hematoxylin eosin (HE) were carried out. Specimens were inspected under a light microscope and adverse effects or signs of inflammation were recorded.

Microangiography

Eight animals (4 controls, 4 treated) were killed after 21 days by means of an i.v. dose of pentobarbital.

Before death the abdominal artery and vein were exposed and an 18-gauge angiocath was inserted and tied in place. A 20 ml syringe containing heparinized saline was used to infuse the abdominal artery. Infusion continued until a clear venous effluent emerged from the transacted abdominal veins. A 100 ml syringe filled with an orange-colored silicone rubber compound (Micro-Fil®, Canton Biomedical, Boulder Colo., U.S.A.) was then injected until orange effluent emerged from the abdominal veins. After the compound had set for 4 hours, the tibiae were separated. The specimens were then sequentially dehydrated according to the cleaning technique of the manufacturer.

Using a scalpel, cross-sections were cut through the mid-portions of the grafts for viewing and slide photography under a dissecting microscope. The absolute number of vessels penetrating the transplant host junction was counted by means of color transparencies (Eppley B et al., J Oral Maxillofac Surg 1988; 46:391–98).

The vessel count was performed in the specimen where the most vessels were observed. Vessels were counted on two separate occasions by the same observers and the results were averaged. If the variation between two values was greater than 10%, a third count was undertaken and the three counts were averaged. Vessel counts in both groups were compared using a paired t-test; P values less than 0.05 were considered significant.

Results

The clinical observations revealed that all wounds healed uneventfully.

Evaluation of Angiogenesis

When counting the vessels, most of them were clearly visible. It was, however, difficult to count the small vessels in the bone-transplant and bone-donor cavity junctions. Because of the variation in the two values by the same observer the third count was undertaken in five specimens.

Donor Cavities

The number of vessels penetrating into the donor cavities was greater in rabbits treated with clodronate than for the control. The results are given in Table I below and the difference is statistically significant (P<0.05).

TABLE I

Number (x) of vessels penetrating donor cavity

|  | x | S.D. | Number of tibiae |
|---|---|---|---|
| Control | 12.3 | 4.6 | 8 |
| Clodronate treated | 26.3 | 4.0 | 8 |

Figure 3:
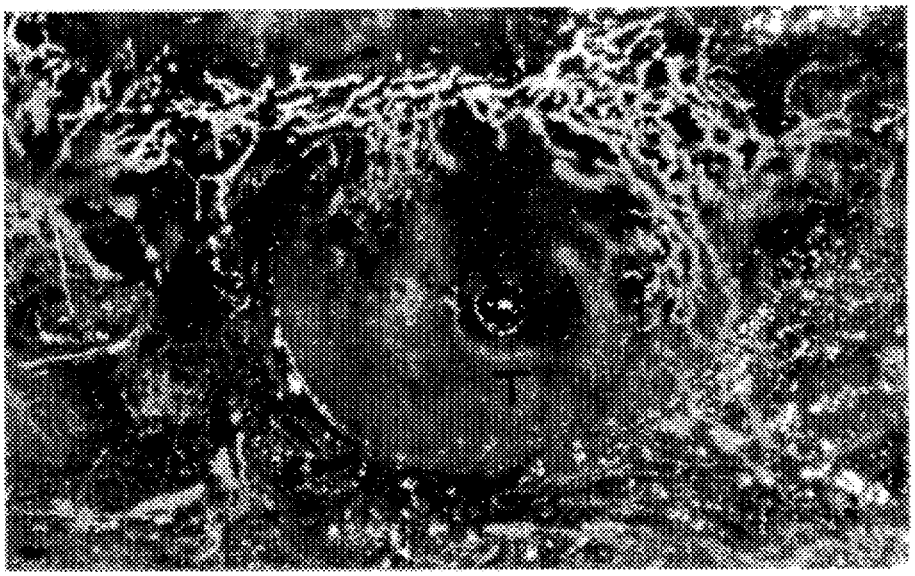
FIG. 3 is a photograph illustrating a 21-day old donor cavity of a rabbit tibia treated with clodronate.
Figure 4:
FIG. 4 is a photograph illustrating a 21-day old donor cavity from an untreated rabbit tibia.

The difference in the amount of vessels can also be observed from the photographs of FIGS. 3 and 4. FIG. 3 discloses a 21-day specimen from a rabbit treated with clodronate. Implant and transplant are located in the centre of the picture. The donor cavity is seen to the right of the transplant. It can be seen that many vessels penetrate the donor cavity and transplant. FIG. 4 shows a 21-day specimen from an untreated rabbit. Only a small number of vessels penetrated the transplant.

Transplants

The transplants in the tibiae from the clodronate-treated animals became vascularized sooner and more extensively than in the tibiae from the control. The difference was statistically significant (P<0.05). The results are presented in Table II.

TABLE II

Number (x) of vessels penetrating transplant

|  | x | S.D. | Number of tibiae |
|---|---|---|---|
| Control | 4.75 | 1.7 | 8 |
| Clodronate treated | 13.0 | 4.0 | 8 |

The vessels penetrated closer to the centre of the cavity in the medicated rabbits than in the control group. In the medicated rabbits the number of vessels from one side of the specimen was greater than from the opposite side.

Histological Findings

No signs of adverse tissue reactions or inflammation were observed when the specimens were studied under the light microscope.

Donor Cavity

The 14-day control specimens exhibited slight collagen formation and were partly devoid of histologically visible elements in the middle part of the cavity. The clodronate-treated specimens exhibited more collagen formation than the control specimens. No empty spaces were seen. At three weeks, the control specimens exhibited only slight bone formation at the outer edges of the cavity. The inner part of the cavity was mainly filled with collagen and a sharp line between the cavity and bone was clearly seen. The clodronate-treated donor cavities were almost completely filled with new bone. Collagen was still found between new bone in the three-week specimens.

Figure 5:
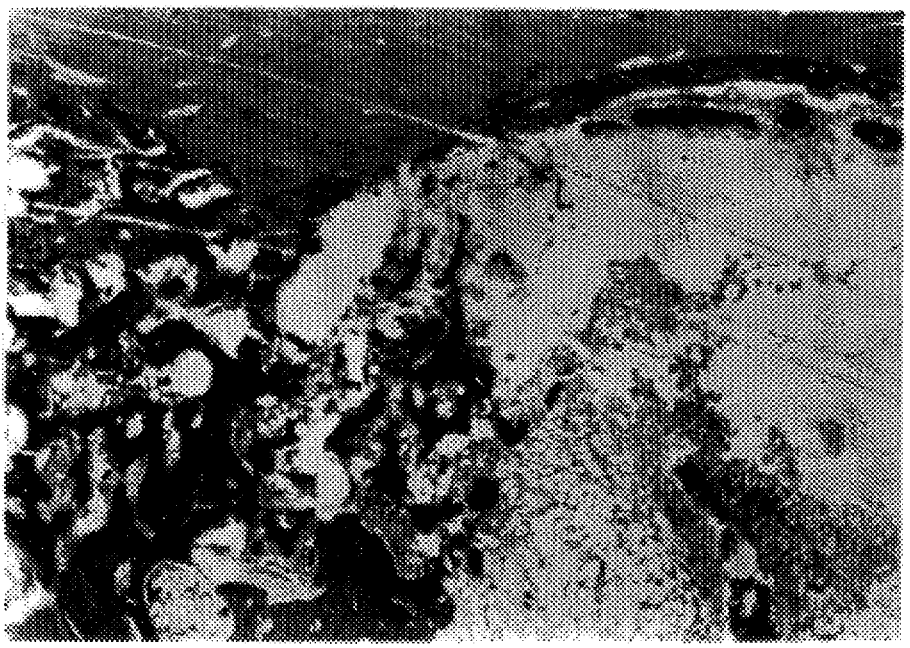
FIG. 5 is a photograph of a five-week old control cavity of a rabbit tibia.
Figure 6:
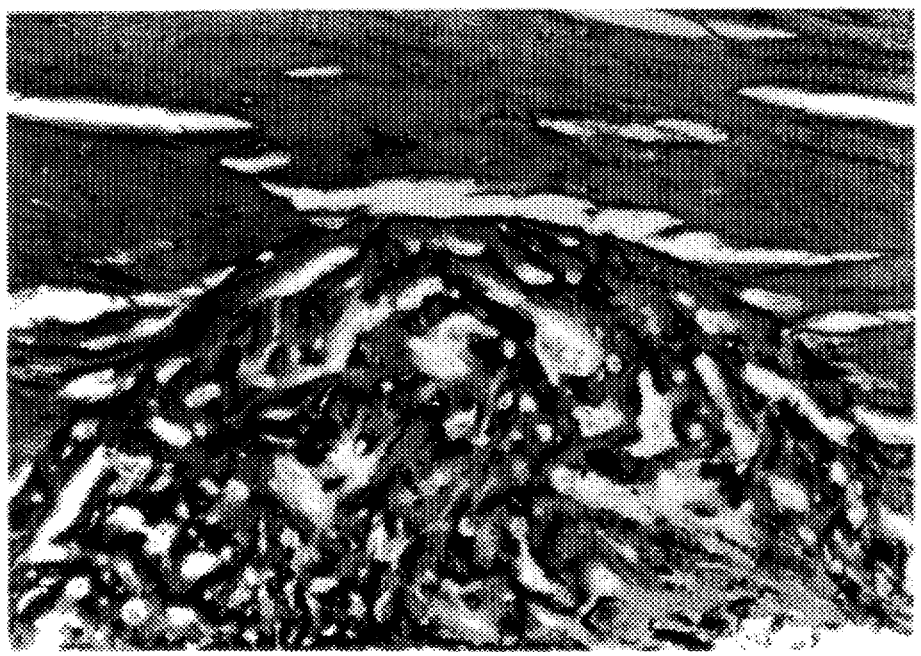
FIG. 6 is a photograph of a five-week old clodronate-treated cavity of a rabbit tibia.
Figure 7:
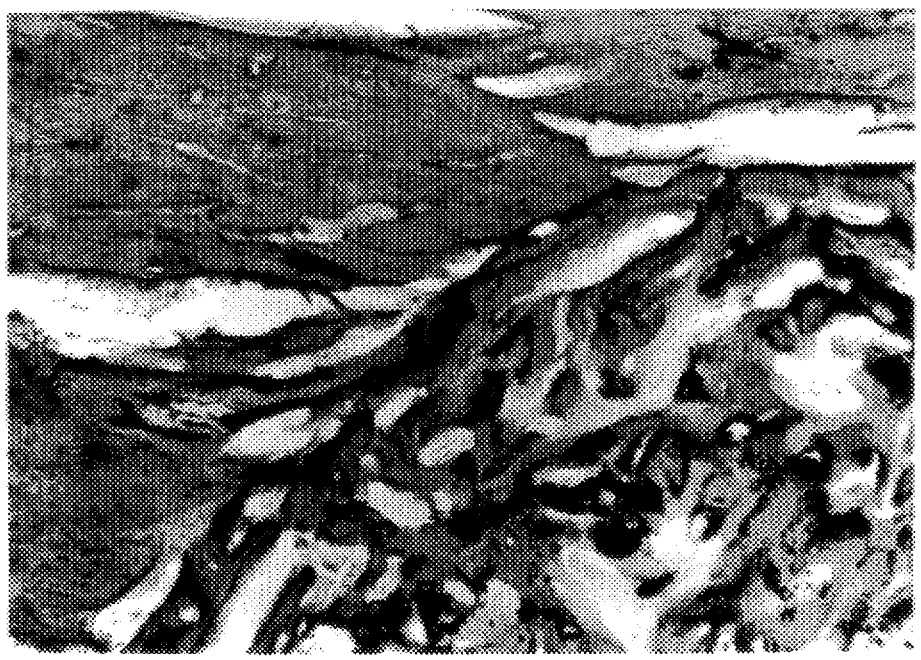
FIGS. 7 and 8 are photographs at greater magnifications of FIG. 6.
Figure 8:

The five-week control cavities were partly filled with new bone, and the line between drilled cavity and bone was still seen in most parts of the cavity. The clodronate-treated cavities were completely filled with new bone and the drilling line was visible but the resolution between the donor cavity and old bone had started. FIG. 5 illustrates a five-week control cavity. Bone regeneration is seen in middle of cavity and in drilling lines. The line between drilled cavity and bone is still seen in most parts of cavity. New bone formation with osteoblasts occurs occasionally in drilling line and also in centre of cavity. FIG. 6 illustrates a five-week clodronate-treated cavity. Cavity is completely filled with new bone and drilling line is still visible but there is a fusion between donor cavity and cortical bone. FIGS. 7 and 8 represent greater magnifications of FIG. 6. In FIG. 7 solid new bone and osteoblasts can be observed. FIG. 8 shows that cortical and new bone are almost completely fused.

Transplants

Figure 9:
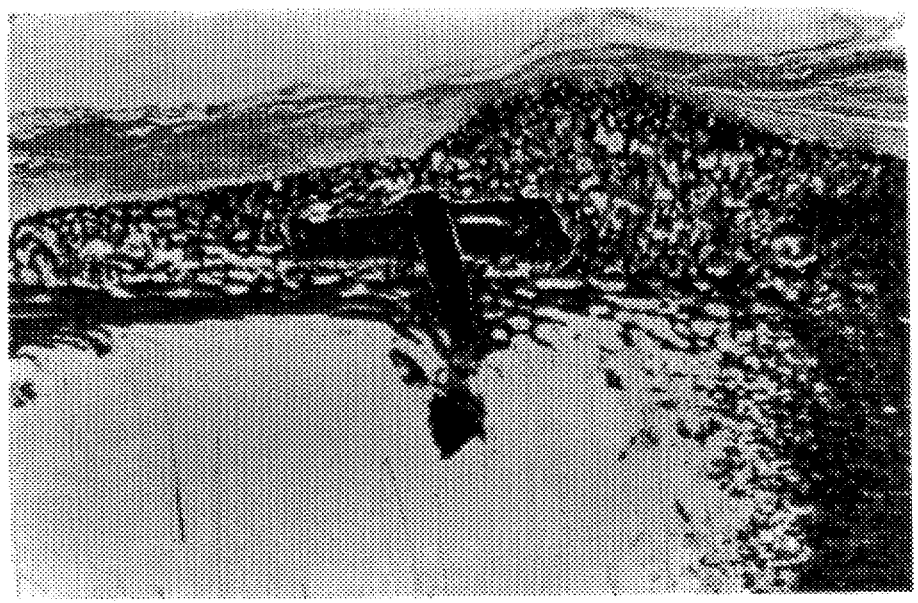
FIG. 9 is a photograph of a side-view of four-week old clodronate-treated rabbit's tibia.

The soft tissue and periosteum above the transplants contained more collagen in the clodronate-treated group than in the control animals at all stages. Fourteen-day control specimens exhibited necrotic bone with invading collagen. Treated transplants were beginning to be resorbed at their outer edges. FIG. 9 represents a side-view of four-week clodronate-treated rabbit's tibia. New bone covers transplant. Periosteum is intact but thinner than that above non-operated area. Implant and transplant are in the middle of this specimen. Donor cavity is to the right from transplant and is the reason for new bone formation in normally empty rabbit's spongious bone.

Figure 10:
FIG. 10 is a photograph of a clodronate-treated 21-day old donor cavity in a rabbit tibia.

Twenty-one-day transplants were partly resorbed. New bone in the resorbed areas was seen in the treated tibiae. No bone formation was seen in control transplants. Bone formation around the implant in the cortical bone area was solid in the clodronate-treated group. FIG. 10 represents a clodronate-treated 21-day specimen. Transplant is partly resorbed and replaced with new bone. The letters A and T represent implant and transplant, respectively, as in FIG. 1, and E represents new bone adjacent to transplant and cortical tibia.

In 35-day specimens there was new bone formation almost throughout the transplants in the treated tibiae. Only solid bone was seen in the control transplants.

Regeneration of transplants occurs through microvascularization of the transplant. In a rat embryo study, Ray (Ray R D, Clin Orthop 1977; 87:43–48) showed that vascularization of a rat embryo takes 3 to 4 weeks. In a review article, Burchardt (Burchardt H, Clin Orthop 1983; 174:28–42) states that cancellous bone differs from cortical grafts as far as rates of revascularization are concerned. He suggested that revascularization of cancellous grafts can occur within hours as a result of end-to-end anastomoses from host vessels. Revascularization may be completed within two weeks (Ray R D; reference as above). A cortical graft is not penetrated by blood vessels until the sixth day (Ray R D; reference as above). Twenty-one days was selected on the basis of the results of a report by Eppley and co-workers (Eppley B et al., J Oral Maxifollfac Surg 1988;

46:391–98) as bone regeneration time after implantation. They found that the vascularization of bone grafts in rabbits reached a maximum after 21 days.

The results of the present study confirm the results of earlier reports (Bonjour J P; Ray R D; both references given above) as far as the control group is concerned. In the medicated rabbits vascularization occurred more quickly than in the control group. The histological findings show clearly that clodronate-treatment makes better bone. The results of the study suggests that bisphosphonates, particularly clodronate, are useful in implant and bone transplant patients where there is a high risk of failure of bone regeneration.

II. Human Tests

Material and Methods

The material of this study were 20 edentulous patients. They all came to the Institute of Dentistry, University of Turku, for an implantation procedure. The Institutional Review Board of the Faculty of Medicine at the University of Turku received the project in order to determine whether human subjects are placed at risk. The unanimous decision made by the Institutional Review Board was that the human subjects concerned in this activity would not be placed at any risk. Patients gave permission for an explantation of an extra implant. 10 patients got a daily dose of 1600 mg clodronate disodium until the extra implant was removed (the medicated group) and 10 patients got placebo. The medication and placebo administration, respectively, started one week before the surgery and continued for three weeks after the surgery.

Surgical Technique

Figure 11:
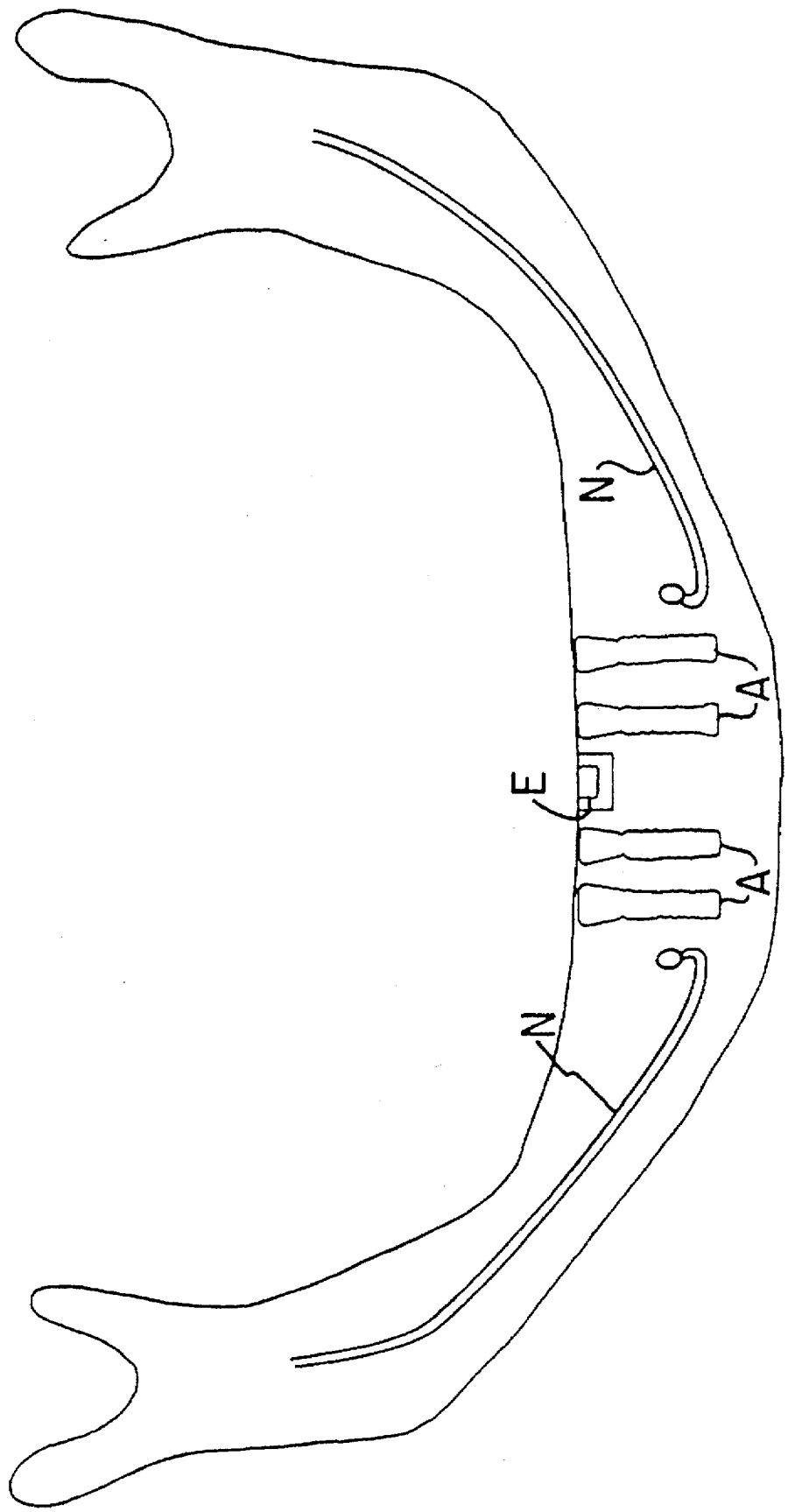
FIG. 11 is a front view of a human mandible with four Astra implants, where A means implants, E explanted implant with bone and N is the mandibular nerve.

Routine method with five Astra implants was used. FIG. 11 is a front view human mandible with four Astra implants, where A means implants, E explanted implant with bone and N is the mandibular nerve. To avoid disturbances in neural function implants are usually placed between the ends of mandibular nerve. At the operation an extra 4 mm screw was installed in the midline of the mandible.

Bone Remodelling

At a separate operation the 4 mm extra implant was removed with a trephan bore after 4 (10 patients, equally from both groups) and 12 weeks (10 patients, equally from both groups). The specimens were imbedded in acrylic blocks and divided in midline in two pieces. To the one piece a histological examination was performed. The other one was taken to a SEM-electromicroscopic examination. Electromicroscopic examination in bone-implant interspace and bone in three points with SEM/EDXA (energy dispersive X-ray analysis) was made. At the four different places, two in the upper cortical bone, one in the middle of the implant and one in the bottom of that the following values are calculated: sodium, calcium, phosphor, magnesium and titan. Calcium/phosphor and calcium/magnesium ratio were calculated in 12 points.

Results

Clinical Treatment

All the wounds healed well. Two patients had problems with their lower denture under the healing period. They were treated by taking away a part denture. No side-effects were recorded. One patient had pain in his hip orthopedic prosthesis. Those disappeared after clodronate medication.

Histological Examinations

One Month-Specimens

Figure 12:
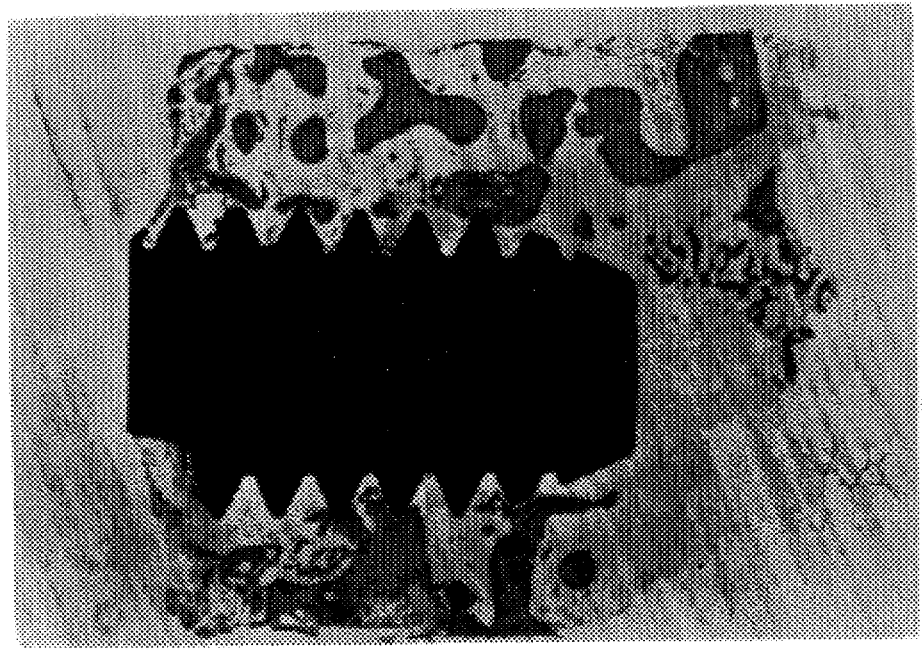
FIG. 12 is a photograph showing the bone-implant specimen corresponding to that marked with E in FIG. 11.
Figure 13:
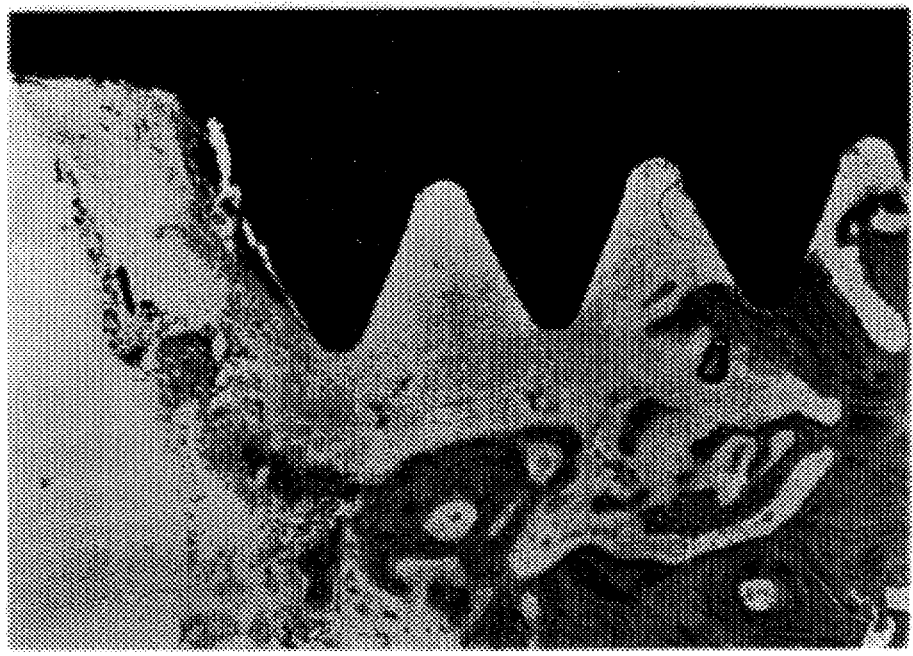
FIG. 13 is a photograph corresponding to FIG. 12 at greater magnification.

Because all the mandibles were considerably resorbed and when the length of explanted implant was 4 mm biopsied bone was cortical in all specimens. The histological results are shown in FIGS. 12 and 13, which both disclose the bone-implant specimen marked with E in FIG. 11. FIG. 13 represents a greater magnification of FIG. 12. No spongious bone was seen. Soft gingival tissue covering the implants was healthy.

Histological examination revealed no more new bone in medicated than control-mandibles. There were no signs of inflammation. The space between implant and bone was mainly filled with collagen. In same points the contact between bone and implant was close. This is natural, because screwed Astra implants were used.

SEM-Results

Figure 14:
FIG. 14 is a scanning election microphotograph of the bone-implant interspace in a human mandible 4 weeks after implantation of an Astra implant.

Table III shows the SEM results in human mandibles 4 weeks after implantation of an extra Astra implant. The 10 000×SEM figure is the same as that FIGS. 11 and 12. The exact points where mineral concentrations are measured are shown with small numbers in FIG. 14. The mean values of those standard points are given in Table III.

TABLE III

|  | CaO | $P_2O_5$ | CaO/$P_2O_5$ | Mg | Na |
| --- | --- | --- | --- | --- | --- |
| control | 56 | 30 | 1.8 | 1.2 | 8.2 |
| medicated | 72 | 40 | 1.8 | 0.9 | 2.8 |

The values are given in weight percent.

Histological and SEM-pictures were similar in both groups. No differences under light and SEM-cross-over pictures were seen. In one month specimens $P_2O_5$ and CaO are both significantly greater in the medicated than in control mandibles. This means that rapid bone formation had begun, osteoclasts have resorbed bone. Osteogenesis is more intensive in medicated than in control patients.

III. Immersion Studies

The effect of bisphosphonates for the treatment of implant surfaces before their use was verified in the following study. Twenty skeletally mature rabbits were used for the implantation of hydroxyapatite coated 6 mm IMZ-implants. Ten rabbits got 25 mg/kg i.m. clodronate in two injections one week before the surgery. Postoperative injections twice a week were continued for 18 days. The remaining ten rabbits did not get any systemic clodronate treatment before or after the surgery. In the operation an IMZ-implant was implanted into both femurs of each rabbit. The implants operated into the right femurs of the rabbits had been immersed for five seconds in a physiological solution containing 6 mg/ml clodronate before the implantation. The implants operated into the left femurs of the rabbits were not treated with clodronate before the implantation. The specimens were analysed according to methods described earlier. SEM examinations were carried out and the total amount of new bone (NB) as well as the amount of bone in contact with the implant (IB, i.e. osseointegration) was determined.

All the wounds of the twenty rabbits healed without infections. Great variations in the NB and IB amounts were found. Preliminary results show that systemic clodronate treatment of the rabbits as well as immersion of the implant in a clodronate solution before the implantation highly enhance the NB and IB formation. The highest NB and IB amounts were received where systemic clodronate treatment of the rabbits were combined with the immersion of the implant in a clodronate solution. Hydroxyapatite coated IMZ implants immersed in a clodronate solution before the implantation into systemically medicated rabbits resulted in a more rapid bone remodelling than implantation of untreated IMZ implants to similarly systemically medicated rabbits.

Figure 15:
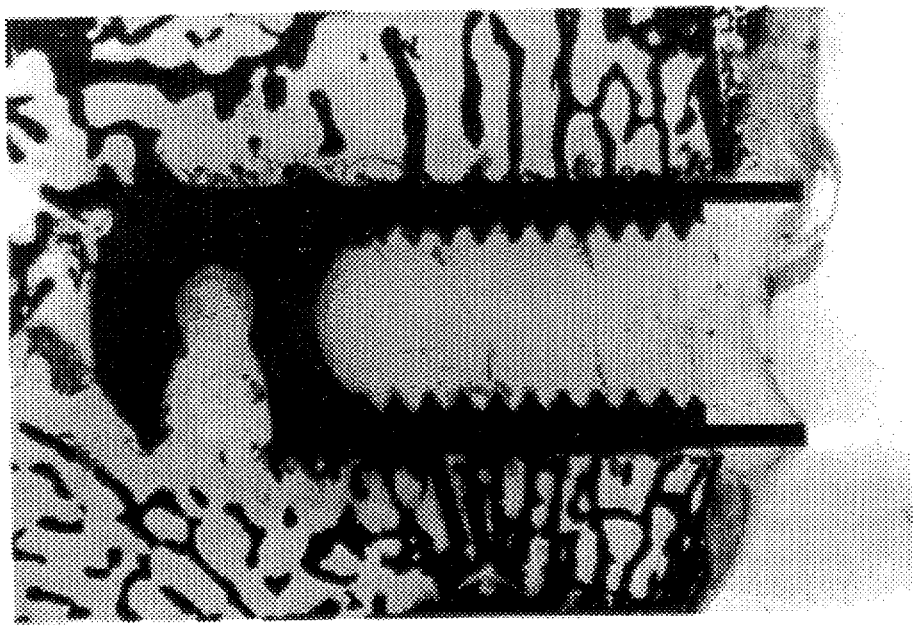
FIG. 15 is a photograph of an untreated implant operated into a nonmedicated rabbit.
Figure 16:
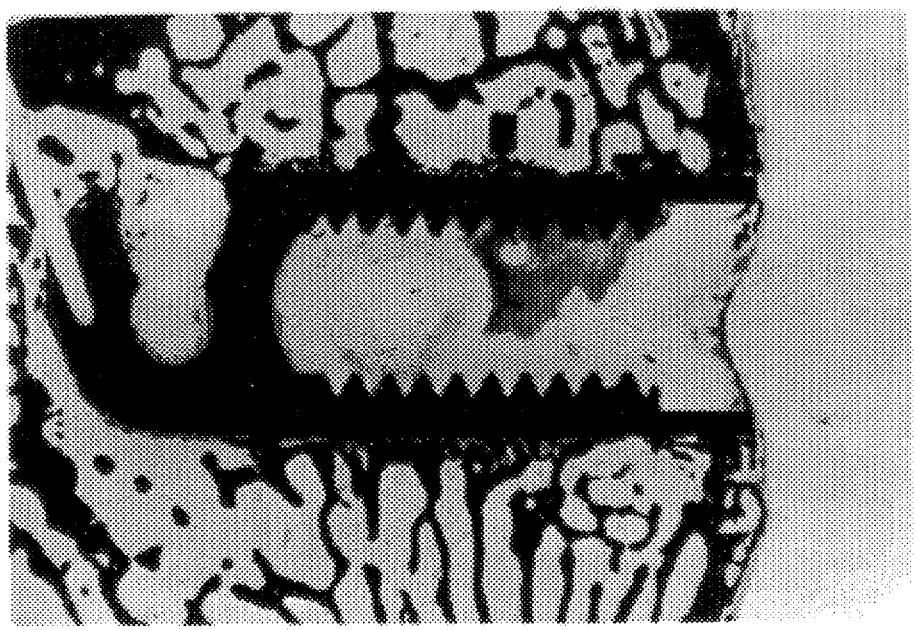
FIG. 16 is a photograph of an immersed implant operated into a systemically medicated rabbit.

FIG. 15 shows an untreated implant operated into a nonmedicated rabbit. FIG. 16 shows an immersed implant operated into a systemically medicated rabbit. The progress of the bone formation is clearly observed in FIG. 16.

I claim:

1. A method of treating endo-osteal materials which includes immersing the endo-osteal material in an aqueous solution comprising an effective amount of a bisphosphonate of the formula (I)

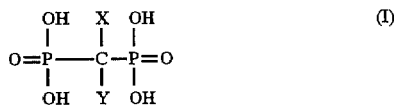

wherein X is H, OH, Cl, F or a methyl group and Y is Cl, OH, —$(CH_2)_2$—$N(CH_3)$—$(CH_2)_4$—$CH_3$, —$(CH_2)_n$—$CH_3$ or —$(CH_2)_n$—$NH_2$, where n is zero or an integer being 1 to 8, —NHZ, where Z is pyridinyl or cycloheptyl, SZ', where Z' is pyridinyl or chlorosubstituted phenyl or Y is a pyridinylsubstituted lower alkyl chain; or a non-toxic, pharmaceutically acceptable salt or ester thereof, after which the endo-osteal material is either removed from the solution, dried and sterilized, or sealed in a vessel, comprising a bisphosphonate solution and sterilized.

2. An endo-osteal material wherein said endo-osteal material is treated with a solution of a bisphosphonate of the formula (I)

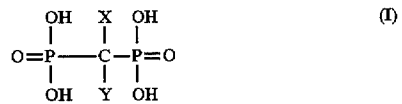

wherein X is H, OH, Cl, F or a methyl group and Y is Cl, OH, —$(CH_2)_2$—$N(CH_3)$—$(CH_2)_4$—$CH_3$, —$(CH_2)_n$—$CH_3$ or —$(CH_2)_n$—$NH_2$, where n is zero or an integer being 1 to 8, —NHZ, where Z is pyridinyl or cycloheptyl, SZ', where Z' is pyridinyl or chlorosubstituted phenyl or Y is a pyridinylsubstituted lower alkyl chain; or a non-toxic, pharmaceutically acceptable salt or ester thereof dissolved in an appropriate solvent.

3. The endo-osteal material according to claim 2 wherein said endo-osteal material is placed in a closed vessel comprising a sterilized solution of a bisphosphonate of the formula (I) or a non-toxic, pharmaceutically acceptable salt or ester thereof dissolved in an appropriate solvent.

4. The endo-osteal material according to claim 2 or 3 wherein said endo-osteal material comprises a metal or metal alloy substrate.

5. The endo-osteal material according to claim 4 wherein said endo-osteal material comprises a substrate of titanium or a titanium based alloy said substrate being coated with a bone-binding layer.

6. The endo-osteal material according to claim 5 wherein said substrate is coated with a layer comprising hydroxyapatite.

7. A endo-osteal material according to claim 2 or 3 wherein said endo-osteal material is a ceramic or glass-ceramic prosthesis.

8. An endo-osteal material according to claim 2 or 3 wherein said bisphosphonate compound is selected from the group consisting of clodronate, pamidronate, etidronate, alendronic acid, neridronic acid, risedroic acid, tiludronate, the bisphosphonate of formula (I) wherein X is H and Y is cycloheptylamino, the bisphosphonate of formula (I) wherein X is OH and Y is —$(CH_2)_2$—$N(CH_3)$—$(CH_2)_4$—$CH_3$, and pharmaceutically acceptable salts and esters of said compounds.

9. The endo-osteal material according to claim 8 wherein said bisphosphonate compound is clodronate or its pharmaceutically acceptable salt or ester.

10. The endo-osteal material according to claim 9 wherein said bisphosphonate compound is clodronate disodium.

11. The endo-osteal material according to claim 9 wherein said bisphosphonate compound is clodronate disodium and the endo-osteal material is a dental implant comprising a substrate of titanium or a titanium based alloy said substrate being coated with a layer comprising hydroxyapatite.

* * * * *